(12) United States Patent
Mukherjee et al.

(10) Patent No.: US 12,144,546 B2
(45) Date of Patent: Nov. 19, 2024

(54) SYSTEMS AND METHODS FOR EYE TRACKING DURING EYE TREATMENT

(71) Applicant: Avedro, Inc., Waltham, MA (US)

(72) Inventors: Amit Mukherjee, Acton, MA (US); Vladimir Ruzhitsky, Newton, MA (US); David Usher, Waltham, MA (US)

(73) Assignee: Avedro, Inc., Waltham, MA (US)

( * ) Notice: Subject to any disclaimer, the term of this patent is extended or adjusted under 35 U.S.C. 154(b) by 798 days.

(21) Appl. No.: 17/278,152

(22) PCT Filed: Sep. 19, 2019

(86) PCT No.: PCT/US2019/051872
§ 371 (c)(1),
(2) Date: Mar. 19, 2021

(87) PCT Pub. No.: WO2020/016274
PCT Pub. Date: Mar. 26, 2020

(65) Prior Publication Data
US 2021/0369108 A1 Dec. 2, 2021

Related U.S. Application Data

(60) Provisional application No. 62/733,620, filed on Sep. 19, 2018.

(51) Int. Cl.
*A61B 3/113* (2006.01)
*A61B 3/00* (2006.01)
*A61F 9/007* (2006.01)

(52) U.S. Cl.
CPC ............ *A61B 3/113* (2013.01); *A61B 3/0008* (2013.01); *A61F 9/007* (2013.01)

(58) Field of Classification Search
CPC ......... A61B 3/113; A61B 3/0008; A61B 3/00; A61F 9/007; A61F 2009/00846;
(Continued)

(56) References Cited

U.S. PATENT DOCUMENTS 4,034,750 A 7/1977 Seiderman
4,665,913 A 5/1987 L'Esperance, Jr.
(Continued)

FOREIGN PATENT DOCUMENTS

CA 2386789 C 1/2009
CN 105960193 A 9/2016
(Continued)

OTHER PUBLICATIONS

Second Japanese Office Action from corresponding Japanese Patent Application No. 2021-515165, mailed Jul. 11, 2023 (with English Translation), 12 pages.
(Continued)

*Primary Examiner* — Tuyen Tra
*Assistant Examiner* — Rahman Abdur
(74) *Attorney, Agent, or Firm* — K&L Gates LLP

(57) ABSTRACT

An example system for tracking motion of an eye during an eye treatment includes an image capture device configured to capture a plurality of images of an eye. The system includes controller(s) including processor(s) that receive the plurality of images from the image capture device. The processor(s) implement a plurality of trackers. Each tracker is configured to detect a respective feature in the plurality of images and provide, based on the respective feature, a respective set of data relating to motion of the eye. The respective features detected by the plurality of trackers are orthogonal relative to each other and the respective sets of data provided by the plurality of trackers are independent of each other. The processor(s) coalesce the sets of data from the plurality of trackers and determine an indicator of the motion of the eye based on the coalesced sets of data.

18 Claims, 10 Drawing Sheets

(58) Field of Classification Search
CPC ... A61F 9/00825; A61F 9/0079; G16H 30/40; G16H 50/20; G06F 3/013; G06F 3/015
USPC .......................................................... 351/209
See application file for complete search history.

(56) References Cited

U.S. PATENT DOCUMENTS

| | | |
|---|---|---|
| 4,712,543 A | 12/1987 | Baron |
| 4,764,007 A | 8/1988 | Task |
| 4,891,043 A | 1/1990 | Zelmer et al. |
| 4,969,912 A | 11/1990 | Kelman et al. |
| 4,994,058 A | 2/1991 | Raven et al. |
| 5,019,074 A | 5/1991 | Muller |
| 5,171,318 A | 12/1992 | Gibson et al. |
| 5,281,211 A | 1/1994 | Parel et al. |
| 5,332,802 A | 7/1994 | Kelman et al. |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,624,437 A | 4/1997 | Freeman et al. |
| 5,779,696 A | 7/1998 | Berry et al. |
| 5,786,893 A | 7/1998 | Fink et al. |
| 5,891,131 A | 4/1999 | Rajan et al. |
| 5,910,110 A | 6/1999 | Bastable |
| 6,033,396 A | 3/2000 | Huang et al. |
| 6,139,876 A | 10/2000 | Kolta |
| 6,161,544 A | 12/2000 | DeVore et al. |
| 6,188,500 B1 | 2/2001 | Rudeen et al. |
| 6,218,360 B1 | 4/2001 | Cintron et al. |
| 6,270,221 B1 | 8/2001 | Liang et al. |
| 6,280,436 B1 | 8/2001 | Freeman et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,394,999 B1 | 5/2002 | Williams et al. |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,617,963 B1 | 9/2003 | Watters et al. |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,331,350 B2 | 2/2008 | Kochevar et al. |
| 7,402,562 B2 | 7/2008 | DeWoolfson et al. |
| 7,731,362 B2 | 6/2010 | Gerlach |
| 7,753,943 B2 | 7/2010 | Strong |
| 7,898,656 B2 | 3/2011 | Yun et al. |
| 7,935,058 B2 | 5/2011 | Dupps et al. |
| RE42,998 E | 12/2011 | Teiwes et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 2001/0055095 A1 | 12/2001 | D'Souza et al. |
| 2002/0013577 A1 | 1/2002 | Frey et al. |
| 2002/0159618 A1 | 10/2002 | Freeman et al. |
| 2002/0164379 A1 | 11/2002 | Nishihara et al. |
| 2003/0175259 A1 | 9/2003 | Karageozian et al. |
| 2003/0189689 A1 | 10/2003 | Rathjen |
| 2003/0231285 A1 | 12/2003 | Ferguson |
| 2004/0002694 A1 | 1/2004 | Pawlowski et al. |
| 2004/0093046 A1 | 5/2004 | Sand |
| 2004/0199079 A1 | 10/2004 | Chuck et al. |
| 2005/0024586 A1 | 2/2005 | Teiwes et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0271590 A1 | 12/2005 | Schwartz et al. |
| 2006/0135957 A1 | 6/2006 | Panescu |
| 2006/0149343 A1 | 7/2006 | Altshuler et al. |
| 2006/0195076 A1 | 8/2006 | Blumenkranz et al. |
| 2006/0276777 A1 | 12/2006 | Coroneo |
| 2007/0024860 A1 | 2/2007 | Tobiason et al. |
| 2007/0048340 A1 | 3/2007 | Bran et al. |
| 2007/0123845 A1 | 5/2007 | Lubatschowski |
| 2007/0135805 A1 | 6/2007 | Peyman |
| 2007/0142828 A1 | 6/2007 | Peyman |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0116096 A1 | 5/2009 | Zalevsky et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0234335 A1 | 9/2009 | Yee |
| 2009/0275929 A1 | 11/2009 | Zickler |
| 2010/0028407 A1 | 2/2010 | Del Priore et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0204584 A1 | 8/2010 | Ornberg et al. |
| 2010/0210996 A1 | 8/2010 | Peyman |
| 2010/0318017 A1 | 12/2010 | Lewis et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0152219 A1 | 6/2011 | Stagni et al. |
| 2011/0190742 A1 | 8/2011 | Anisimov |
| 2011/0202114 A1 | 8/2011 | Kessel et al. |
| 2011/0208300 A1 | 8/2011 | Eugene et al. |
| 2011/0237999 A1 | 9/2011 | Muller et al. |
| 2011/0264082 A1 | 10/2011 | Mrochen |
| 2011/0288466 A1 | 11/2011 | Muller et al. |
| 2011/0301524 A1 | 12/2011 | Bueler et al. |
| 2012/0083772 A1 | 4/2012 | Rubinfield et al. |
| 2012/0215155 A1 | 4/2012 | Muller et al. |
| 2012/0203161 A1 | 8/2012 | Herekar |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2013/0211387 A1 | 8/2013 | Riedel et al. |
| 2014/0049750 A1 | 2/2014 | Grecu et al. |
| 2014/0194957 A1 | 7/2014 | Rubinfield et al. |
| 2014/0249509 A1 | 9/2014 | Rubinfield et al. |
| 2015/0061995 A1 | 3/2015 | Gustafsson et al. |
| 2015/0310253 A1 | 10/2015 | Agrawal et al. |

FOREIGN PATENT DOCUMENTS

| | | |
|---|---|---|
| CN | 106462236 A | 2/2017 |
| DE | 102008046834 | 3/2010 |
| EP | 1561440 | 8/2005 |
| EP | 1790383 | 5/2007 |
| IT | MI2010A001236 | 5/2010 |
| KG | 1376 | 8/2011 |
| RU | 2086215 | 8/1997 |
| RU | 2420330 | 6/2011 |
| RU | 2456971 | 7/2012 |
| WO | 2000074648 | 12/2000 |
| WO | 2001058495 | 8/2001 |
| WO | 2005/094667 A2 | 10/2005 |
| WO | 2005110397 | 11/2005 |
| WO | 2006012947 | 2/2006 |
| WO | 2006128038 | 11/2006 |

(56) References Cited

FOREIGN PATENT DOCUMENTS

| | | |
|---|---|---|
| WO | 2007001926 | 1/2007 |
| WO | 2007053826 | 5/2007 |
| WO | 2007120457 | 10/2007 |
| WO | 2007139927 | 12/2007 |
| WO | 2007143111 | 12/2007 |
| WO | 2008000478 | 1/2008 |
| WO | 2008052081 | 5/2008 |
| WO | 2008095075 | 8/2008 |
| WO | 2009073213 | 6/2009 |
| WO | 2009114513 | 9/2009 |
| WO | 2009146151 | 12/2009 |
| WO | 2010/000280 A1 | 1/2010 |
| WO | 2010011119 | 1/2010 |
| WO | 2010015255 | 2/2010 |
| WO | 2010023705 | 3/2010 |
| WO | 2010093908 | 8/2010 |
| WO | 2011019940 | 2/2011 |
| WO | 2011116306 | 9/2011 |
| WO | 2012004726 | 1/2012 |
| WO | 2012149570 | 11/2012 |
| WO | 2012174453 | 12/2012 |
| WO | 2013148713 | 10/2013 |
| WO | 2013148895 | 10/2013 |
| WO | 2013148896 | 10/2013 |
| WO | 2013149075 | 10/2013 |
| WO | 2014202736 | 12/2014 |

OTHER PUBLICATIONS

Office Action for related Japanese Application No. 2021-515165; action dated Oct. 25, 2022; (9 pages).

International Search Report mailed on Dec. 26, 2019, issued in connection with International Application No. PCT/US2019/051872, filed on Sep. 19, 2019, 2 pages.

Written Opinion mailed on Dec. 26, 2019, issued in connection with International Application No. PCT/US2019/051872, filed on Sep. 19, 2019, 4 pages.

Extended European Search Report for related European Application No. 19861991.8; action dated May 19, 2022; (8 pages).

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164 (6 pages).

Averianova, O. S., "Nastoyaschee I buduschee kross-linkage." Mir Ofalmologii, 2010, [online] [retrieved on Feb. 13, 2014] Retrieved from the internet: http:/ /miroft.org.ua!publications/.html.

Baier J. et al., "Singlet Oxygen Generation by UVA Light Exposure of Endogenous Photosensitizers," Biophysical Journal, vol. 91(4), pp. 1452-1459; Aug. 15, 2006 (8 pages).

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969 (7 pages).

Barbarino, S. et al., "Post-LASIK ectasia: Stabilization and Effective Managmeent with Riboflavin / ultraviolet A-induced collagen cross-linking," Association for Research in Vision and Ophthalmology, 2006 (1 page).

Bruel, A., "Changes in Biomechanical Properties, Composition of Collagen and Elastin, and Advanced Glycation Endproducts of the Rat Aorta in Relation to Age," Atherosclerosis 127, Mar. 14, 1996 (11 pages).

Chace, K.V. et al., Abstract for "The role of nonenzymatic glycosylation, transition metals, and free radicals in the formation of collagen aggregates", Arch Biochem Biophys., Aug. 1, 1991, 288(2) pp. 473-480 (1 page).

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238 (8 pages).

Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008 (10 pages).

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011 (3 pages).

Coskenseven E. et al., "Comparative Study of Corneal Collagen Cross-linking With Riboflaving and UVA Irradiation in Patients With Keratoconus," Journal of Refractive Surgery, vol. 25, issue 4, pp. 371-376; Apr. 2009 (6 pages).

Erskine H., "Avedro Becomes Sponsor of US FDA Clinical Trials of Corneal Collagen Crosslinking," Press Release, Mar. 16, 2010 (1 page).

Fite et al. Noninvasive Multimodal Evaluation of Bioengineered Cartilage Constructs Combining Time-Resolved Fluorescence and Ultrasound Imaging. Tissue Eng: Part C vol. 17, No. 4, 2011 (10 pages).

Friedman, M. et al. "Advanced Corneal Cross-Linking System with Fluorescence Dosimetry", Journal of Ophthalmology, vol. 2012, Article ID 303459, dated May 7, 2012 (6 pages).

Gibson, Q. et al., "The Oxidation of Reduced Flavin Mononucleotide by Molecular Oxygen," Biochem. J. (1962) 83, 368-377 (10 pages).

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009 (11 pages).

Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009 (4 pages).

Hitzenberger et al., "Birefringence Properties of the Human Cornea Measured With Polarization Sensitive Optical Coherence Tomography," Bull. Soc. Beige Ophtalmol., 302, 153-168, 2006.

Holmstrom, B. et al., "Riboflavin as an Electron Donor in Photochemical Reactions," 1867-1871, Nov. 29, 1960 (5 pages).

IMEX, "KXL System: Crosslinking Para Cirugia Corneal Bibliografia Cientifica," Product Literature, Nov. 23, 2010 (24 pages).

Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).

Kampik D. et al., "Influence of Corneal Collagen Crosslinking With Riboflavin and Ultraviolet-A Irradiation on Excimer Laser Surgery," Investigative Opthalmology & Visual Science, vol. 51, No. 8, pp. 3929-3934; Aug. 2010 (6 pages).

Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.

Kanellopoulos, A. J., "Keratoconus management: UV A-induced collagen cross-linking followed by a limited topo-guided surface excimer ablation," American Academy of Ophthalmology, 2006 (25 pages).

Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).

Kissner Anja, et al., "Pharmacological Modification of the Epithelial Permeability by Benzalkonium Chloride in JVNRiboflavin Corneal Collagen Cross-Linking," Current Eye Research 35(8), pp. 715-721; Mar. 2010 (7 pages).

Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, val. 224, No. 9, pp. 700-706; Sep. 2007 (7 pages).

Koller, T. et al., "Complication and failure rates after corneal crosslinking," Journal Cataract and refractive surgery, vol. 35, No. 8, Aug. 2009, pp. 1358-1362.

Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pts. 17-26).

(56) References Cited

OTHER PUBLICATIONS

Krueger Ronald R., "Rapid VS Standard Collagen CXL with Equivalent Energy Dosing," presentation slides, (26 pages); available at http://www.slideshare.net/logen/krueger-kerekar-rapid-cross-linking (date unknown, prior to Nov. 9, 2009).

Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).

Li, C. et al. "Noncontact All-Optical Measurement of Corneal Elasticity." Optics Letters. vol. 37, No. 10, May 15, 2012 (pp. 1625-1627).

Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).

Marzouky, et. al., Tensioactive-mediated Transepithelial Corneal Cross-linking—First Laboratory Report, European Ophthalmic Review, 2009, 3(2), pp. 67-70.

Massey, V., "Activation of Molecular Oxygen by Flavins and Flavoproteins," The Journal of Biological Chemistry vol. 269, No. 36, Issue of Sep. 9, pp. 22459-22462, 1994 (4 pages).

Meek, K.M. et al. "The Cornea and Sclera", Collagen: Structure and Mechanics, Chapter 13, pp. 359-396, 2008 (38 pages).

Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).

Muller L., et al., "The Specific Architecture of the Anterior Stroma Accounts for Maintenance of Corneal Curvature," Br. J. Opthalmol., vol. 85, pp. 437-443; Apr. 2001 (8 pages).

Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).

O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).

Pinelli R., et al., "C3-Riboflaving Treatments: Where Did We Come From? Where Are We Now?" Cataract & Refractive Surgery Today Europe, Summer 2007, pp. 36-46; Jun. 2007 (10 pages).

Pinelli, R. "Corneal Cross-Linking with Riboflavin: Entering a New Era in Ophthalmology." Ophthalmology Times Europe. vol. 2, No. 7, Sep. 1, 2006 (3 pages).

Pinelli, R., "Panel Discussion: Epithelium On/Off, Corneal abrasion for CCL contra", presented at the 3° International Congress of Corneal Cross Linking on Dec. 7-8, 2007 in Zurich (36 pages).

Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).

Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).

Randall, J. et al., "The Measurement and Intrepretation of Brillouin Scattering in the Lens of the Eye," The Royal Society, Abstract only, published 2013 [available online at http://rspb.royalsocietypublishing.org/content/214/11971449.short] (1 page).

Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].

Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).

Rocha K., et al., "Comparative Study of Riboflavin-UVA Cross-linking and "Flash-linking" Using Surface Wave Elastometry," Journal of Refractive Surgery, vol. 24 Issue 7, pp. S748-S751; Sep. 2008 (4 pages).

Rolandi et al. Correlation of Collagen-Linked Fluorescence and Tendon Fiber Breaking Time. Gerontology 1991;27:240-243 (4 pages).

Scarcelli, G. et al., "Brillouin Optical Microscopy for Corneal Biomechanics", Investigative Ophthalmology & Visual Science, Jan. 2012, vol. 53, No. 1, pp. 185-190 (6 pages).

Sheehan M., et al., "Illumination System for Corneal Collagen Crosslinking," Optometry and Vision Science, vol. 88, No. 4, pp. 512-524; Apr. 2011 (13 pages).

Spoerl E. et al., "Safety of UVA-Riboflavin Cross-Linking of the Cornea," Cornea, vol. 26, No. 4, pp. 385-389; May 2007 (5 pages).

Spoerl E., et al., "Artificial Stiffening of the Cornea by Induction of Intrastromal Cross-links," Oer Ophthalmologe, vol. 94, No. 12, pp. 902-906; Dec. 1997 (5 pages).

Spoerl E., et al., "Induction of Cross-links in Corneal Tissue," Experimental Eye Research, vol. 66, Issue 1, pp. 97-103; Jan. 1998 (7 pages).

Spoerl E., et al., "Techniques for Stiffening the Cornea," Journal of Refractive Surgery, vol. 15, Issue 6, pp. 711-713; Nov.-Dec. 1999 (4 pages).

Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).

Thorton, I. et al., "Biomechancial Effects of Intraocular Pressure Elevation on Optic Berve/Lamina Cribrosa before and after Peripapillary Scleral Collagen Cross-Linking." Invest. Ophthalmol. Vis. Sci., Mar. 2009, 50(3): pp. 1227-1233.

UV-X: Radiation System for Treatment of Keratokonus, PESCHKE Meditrade GmbH; retrieved from http://www.peschkemed.ch/ on Sep. 27, 2011 (1 page) (date unknown, prior to Sep. 16, 2008).

Vasan S., et al., "An agent cleaving glucose-derived protein crosslinks in vitro and in vivo;" Letters to Nature, vol. 382, pp. 275-278; Jul. 18, 1996 (4 pages).

Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).

Wollensak G., "Crosslinking Treatment of Progressive Keratoconus: New Hope," Current Opinion in Ophthalmology, vol. 17(4), pp. 356-360; Aug. 2006 (5 pages).

Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).

Wollensak G., et al., "Collagen Crosslinking of Human and Porcine Sclera," J. Cataract Refract. Surg., vol. 30, Issue 3, pp. 689-695; Mar. 2004 (7 pages).

Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).

Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).

Wong, J. et al., "Post-Lasik ectasia: PRK following previous stablization and effective management with Riboflavin I ultraviolet A-induced collagen cross-linking," Association for Research in Vision and Ophthalmology, 2006 (1 page).

Yang H., et al., "3-D Histomorphometry of the Normal and Early Glaucomatous Monkey Optic Nerve Head: Lamina Cribrosa and

(56) References Cited

OTHER PUBLICATIONS

Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970).
Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 5, 2011 (pp. 13011-13022).
International Patent Application No. PCT/US2019/051872, International Search Report, Dec. 26, 2019 (2 pages).
International Patent Application No. PCT/US2019/051872, Written Opinion of the ISA, Dec. 26, 2019 (4 pages).
First Chinese Office Action and English Translation from corresponding Chinese Patent Application No. 201980071362.0, dated Jan. 17, 2024. 22 pages.

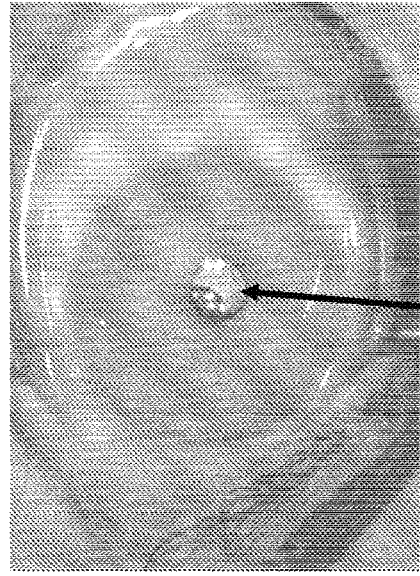
FIG. 9D graying of pupil 90d
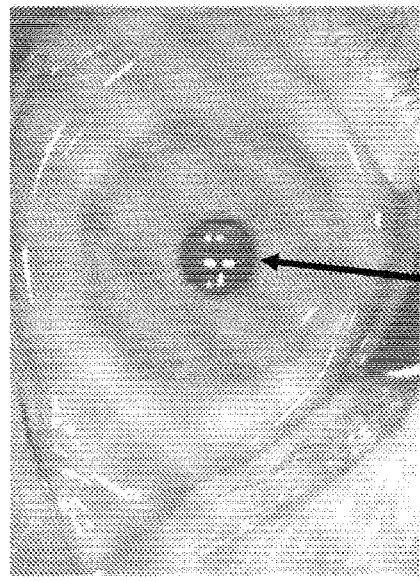
FIG. 9E erratic reflection patterns due to IOL 90e
FIG. 9F occlusion (e.g., finger) 90f

SYSTEMS AND METHODS FOR EYE TRACKING DURING EYE TREATMENT

CROSS-REFERENCE TO RELATED APPLICATIONS

This application is the US national phase under 35 U.S.C. § 371 of international application PCT/US2019/051872, filed Sep. 19, 2019, which claims the benefit of U.S. Provisional Patent Application No. 62/733,620, filed Sep. 19, 2018, the contents of which are incorporated entirely herein by reference.

BACKGROUND

Field

The present disclosure pertains to systems and methods for eye treatments, and more particularly, to systems and methods that track eye movement to deliver treatment to desired areas of the eye.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

Cross-linking treatments may also be employed to induce refractive changes in the cornea to correct disorders such as myopia, hyperopia, astigmatism, irregular astigmatism, presbyopia, etc.

SUMMARY

Because a cross-linking procedure might require exposing the cornea to the photoactivating light for at least several minutes, e.g., one to thirty minutes, some eye movement is very likely to occur during the procedure. To address the occurrence of eye movement, systems and methods can employ an eye tracking system to determine any changes in the position of the cornea and, in response, adjust an illumination system to apply photoactivating light precisely to specified areas of the cornea.

An example system for tracking motion of an eye during an eye treatment includes an image capture device configured to capture a plurality of images of an eye. The system includes one or more controllers including one or more processors configured to execute program instructions stored on one or more computer readable media. The one or more processors receive the plurality of images from the image capture device. The one or more processors implement a plurality of trackers. Each tracker is configured to detect a respective feature in the plurality of images and provide, based on the respective feature, a respective set of data relating to motion of the eye. The respective features detected by the plurality of trackers are orthogonal relative to each other and the respective sets of data provided by the plurality of trackers are independent of each other. The one or more processors coalesce the sets of data from the plurality of trackers and determine an indicator of the motion of the eye based on the coalesced sets of data.

Eye tracking in medical treatments, such as cross-linking treatments, should be robust and accurate, because an error in eye tracking can result in ineffective treatment and/or damage/injury to the patient. Example systems and methods are highly robust, because the trackers obtain information on orthogonal (non-overlapping) image features in the plurality of images and provide independent estimates of eye motion. These independent estimates are analyzed against each other using to reduce error variance and allow a smooth estimate of eye motion to be obtained with greater accuracy. If the trackers occasionally fail due to reflections and other obstructions in the images, the systems and methods can account for erroneous and missing information from such failures, thereby allowing tracking to continue.

BRIEF DESCRIPTION OF THE DRAWINGS

FIG. 9D illustrates an example image capturing graying of a pupil caused by an intra-ocular implant as a possible error-inducing phenomenon.

FIG. 9E illustrates an example image capturing an erratic reflection pattern due to an implanted intra-ocular lens as a possible error-inducing phenomenon.

FIG. 9F illustrates an example image capturing an occlusion, such as a finger or an eye dropper, as a possible error-inducing phenomenon.

Figure 1:
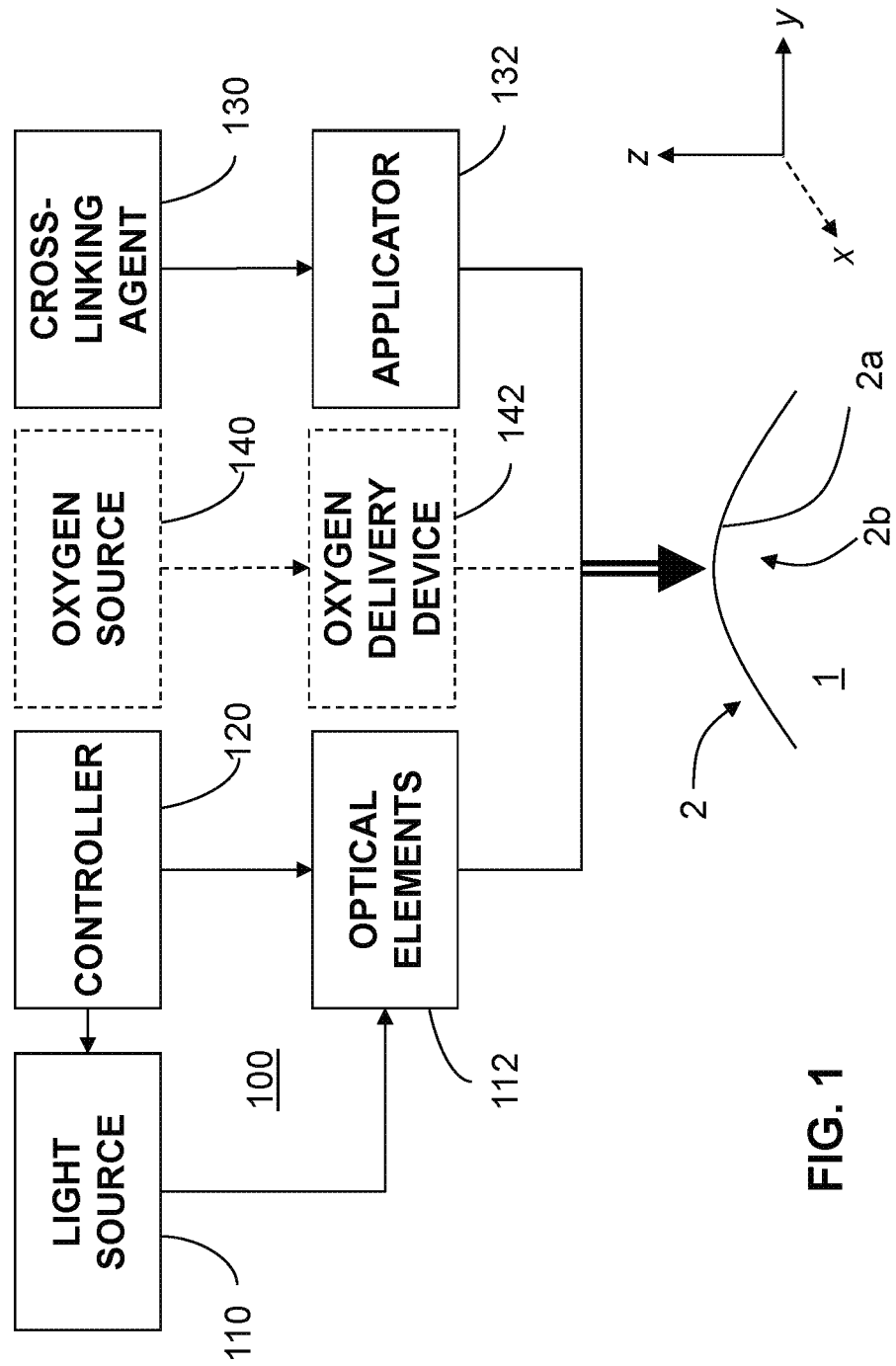
FIG. 1 illustrates an example system that delivers a cross-linking agent and photoactivating light to a cornea of an eye in order to generate cross-linking of corneal collagen, according to aspects of the present disclosure.

While the present disclosure is susceptible to various modifications and alternative forms, a specific embodiment thereof has been shown by way of example in the drawings and will herein be described in detail. It should be understood, however, that it is not intended to limit the present disclosure to the particular forms disclosed, but on the contrary, the intention is to cover all modifications, equivalents, and alternatives falling within the spirit of the present disclosure.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. Example systems and methods for applying the cross-linking agent is described in U.S. Pat. No. 10,342,697, filed Apr. 13, 2017 and titled "Systems and Methods for Delivering Drugs to an Eye," the contents of which are incorporated entirely herein by reference.

The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may include ultraviolet A (UVA) (e.g., approximately 365 nm) light. Alternatively, the photoactivating light may include another wavelength, such as a visible wavelength (e.g., approximately 452 nm). As described further below, corneal cross-linking improves corneal strength by creating chemical bonds within the corneal tissue according to a system of photochemical kinetic reactions. For instance, riboflavin and the photoactivating light may be applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for photoactivating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a microelectromechanical system (MEMS) device, e.g., a digital micro-mirror device (DMD), to modulate the application of photoactivating light spatially and temporally. Using DMD technology, the photoactivating light from the light source 110 is projected in a precise spatial pattern that is created by microscopically small mirrors laid out in an array on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Aspects of a dosimetry system are described in further detail below. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than light of shorter wavelengths. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, the irradiance and the dose of photoactivating light affect the amount and the rate of cross-linking.

When the cross-linking agent 130 is riboflavin in particular, the UVA light may be applied continuously (continuous wave (CW)) or as pulsed light, and this selection has an effect on the amount, the rate, and the extent of cross-linking. If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for instance, may involve combinations of myopia, hyperopia, astigmatism, irregular astigmatism, presbyopia and complex corneal refractive surface corrections because of ophthalmic conditions such as keratoconus, pellucid marginal disease, post-LASIK ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Pat. No. 9,707,126, filed Oct. 31, 2012 and titled "Systems and Methods for Corneal Cross-Linking with Pulsed Light," the contents of these applications being incorporated entirely herein by reference. Additionally, an example mask device for delivering concentrations of oxygen as well as photoactivating light in eye treatments is described in U.S. Patent Application Publication No. 2017/0156926, filed Dec. 5, 2016 and titled "Systems and Methods for Treating an Eye with a Mask Device," the contents of which are incorporated entirely herein by reference. For instance, a mask may be placed over the eye(s) to produce a consistent and known oxygen concentration above the surface.

When riboflavin absorbs radiant energy, especially light, it undergoes photoactivation. There are two photochemical kinetic pathways for riboflavin photoactivation, Type I and Type II. The reactions involved in both the Type I and Type II mechanisms and other aspects of the photochemical kinetic reactions generating cross-linking activity are described in U.S. Pat. No. 10,350,111, filed Apr. 27, 2016 and titled "Systems and Methods for Cross-Linking Treatments of an Eye," the contents of which are incorporated entirely herein by reference.

To treat keratoconus or to achieve refractive correction for instance, an effective cross-linking procedure applies photoactivating light as precisely as possible to specified areas of a cornea treated with a cross-linking agent. Application of the photoactivating light outside the specified areas might generate undesired structural changes or damage in the cornea and might negatively affect treatment results. Precise application of the photoactivating light, however, may be difficult to achieve due to eye movement that may occur during the procedure. Such eye movement, for instance, might include translation along the x-y plane as shown in FIG. 1, changes in gaze angle, and/or bulk head motion. (In FIG. 1, the depth of the cornea 2 is measured along a z-axis and patterns of photoactivating light may be projected on transverse x-y planes.) Because a cross-linking procedure might require exposing the cornea to the photoactivating light for at least several minutes, e.g., one to thirty minutes, some eye movement is very likely to occur during the procedure.

Figure 2:
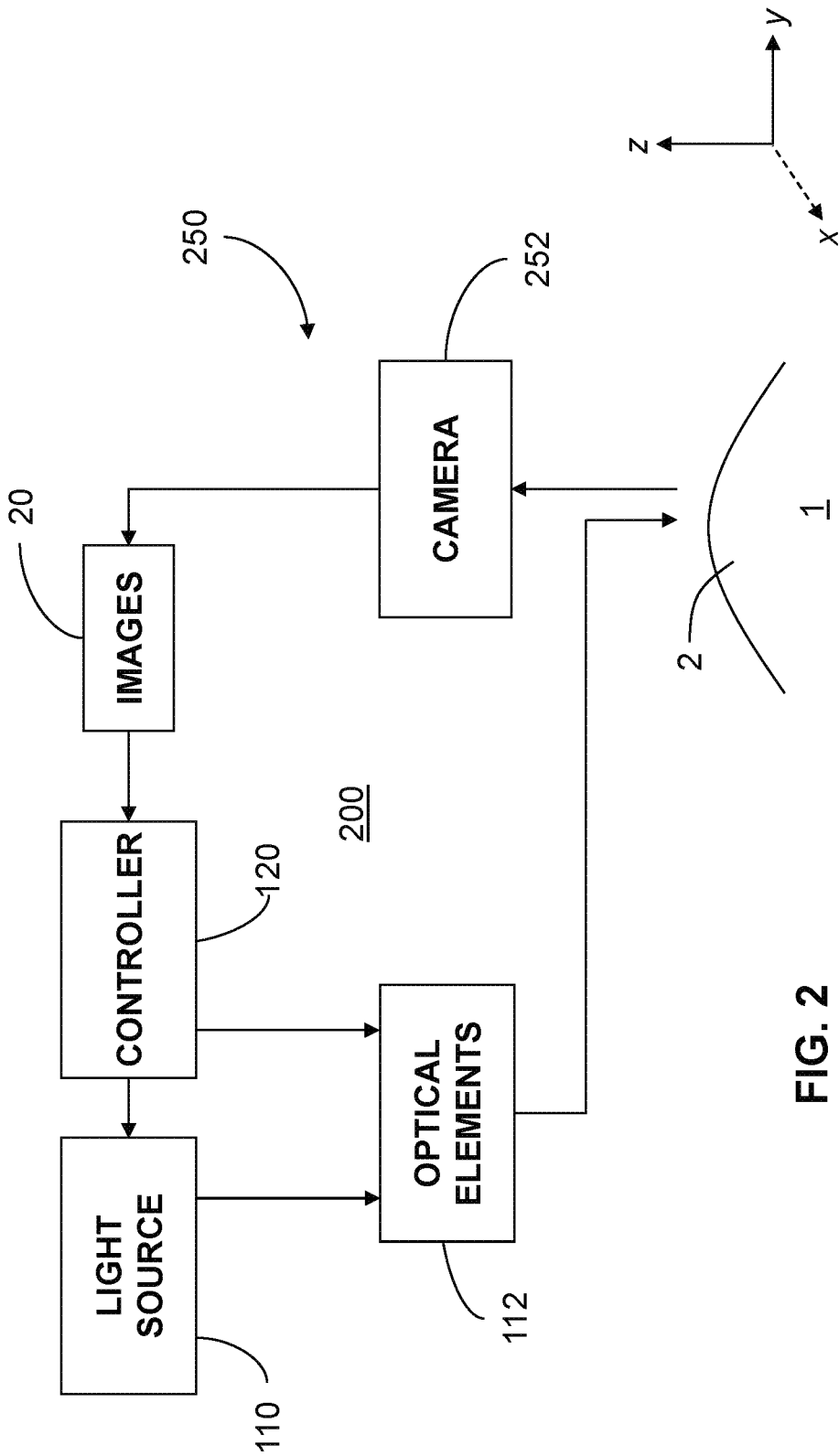
FIG. 2 illustrates an example treatment system with an eye tracking system, according to aspects of the present disclosure.

To address the occurrence of eye movement, embodiments can employ an eye tracking system to determine any changes in the position of the cornea and, in response, adjust the illumination system to apply photoactivating light precisely to specified areas of the cornea. FIG. 2 illustrates an example treatment system 200 with an eye tracking system 250. The treatment system 200 includes an illumination system for directing photoactivating light to the cornea 2 of the eye 1. The illumination system includes the light source 110 and the optical elements 112 as described above. The light source 110, for instance, may include one or more LED's that emit UV light to photoactivate riboflavin that has been applied to the cornea 2. The optical elements 112 project the photoactivating light in a precise spatial pattern onto the cornea 2 along an x-y plane. Additionally, the treatment system 200 includes one or more controllers 120 to control aspects of the treatment system 200.

The eye tracking system 250 includes a camera 252 (image capture device) that dynamically captures a plurality of images 20 of the eye 1 during a procedure. Each image 20 may correspond to one of a series of frames in a video of the eye 1 in motion. In some embodiments, the camera 252 may be a high-speed infrared camera and the images 20 may be pixelated digital images. In general, the controller(s) 120 can process the images 20 to detect a position of one or more geometric features of the eye 1 relative to the camera 252, and thus the treatment system 200. Using the position of one or more features as reference(s), the controller(s) 120 can determine the location of the specified areas of the cornea 2. Thus, the controller(s) 120 can adjust the treatment system 200 to deliver the photoactivating light to the location of the specified areas. The eye tracking system 250 also includes the software (e.g., computer-readable instructions stored on a non-transitory medium) employed by the controller(s) 120 to process the images 20.

Figure 3:
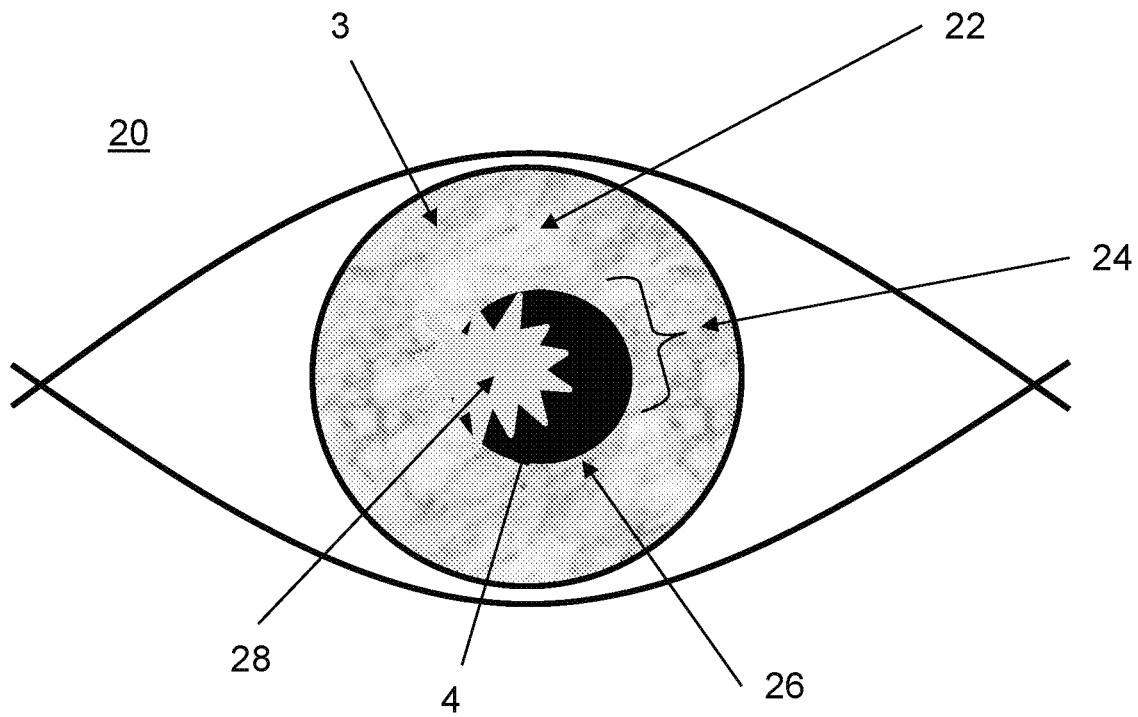
FIG. 3 illustrates features that can be detected in pixelated images of an eye captured by an example eye tracking system, according to aspects of the present disclosure.

As described above, eye tracking in medical treatments, such as cross-linking treatments, should be robust and accurate, because an error in eye tracking can result in ineffective treatment and/or damage/injury to the patient. Some eye tracking systems may rely on reflections of light from the cornea that are captured in images of the eye. FIG. 3 illustrates an example reflection 28, for instance. Reflection patterns, however, can provide an unreliable basis for eye tracking. As shown in FIG. 9E, for instance, an intraocular lens (IOL) implanted in the eye can generate erratic reflection patterns. Additionally, the tear-film on the cornea may break up when the eye is kept open for a prolonged period of time by a speculum that is employed to restrict eye blinking during a treatment. The dry and broken tear-film creates a reflection surface that produces bright patterns in images and poses further challenges for reflection-based tracking systems. Accordingly, to achieve robust and accurate eye tracking, embodiments employ approaches that do not rely on reflections of light from the cornea.

FIG. 3 illustrates an example pixelated image 20 of an eye captured by the camera 252. In particular, the image 20 includes features 22, 24, 26. Image feature 22 corresponds to low-level anatomical structures in an iris region 3 formed by iris-sphincter muscles and pigmented fibrovascular stroma. These anatomical structures appear as textures in the images 20, particularly when captured by a high-speed infrared camera. Image feature 24 corresponds to a dark substantially circular or circle-like shape defined by a contrast between the iris region 3 and the pupil region 4. Image feature 26 corresponds to the substantially circular boundary between the iris region 3 and the pupil region 4. The controller(s) 120 can detect the image features 22, 24, 26 and determine changes in the shapes and positions of the image features 22, 24, 26 over a time series of images 20.

Figure 4:
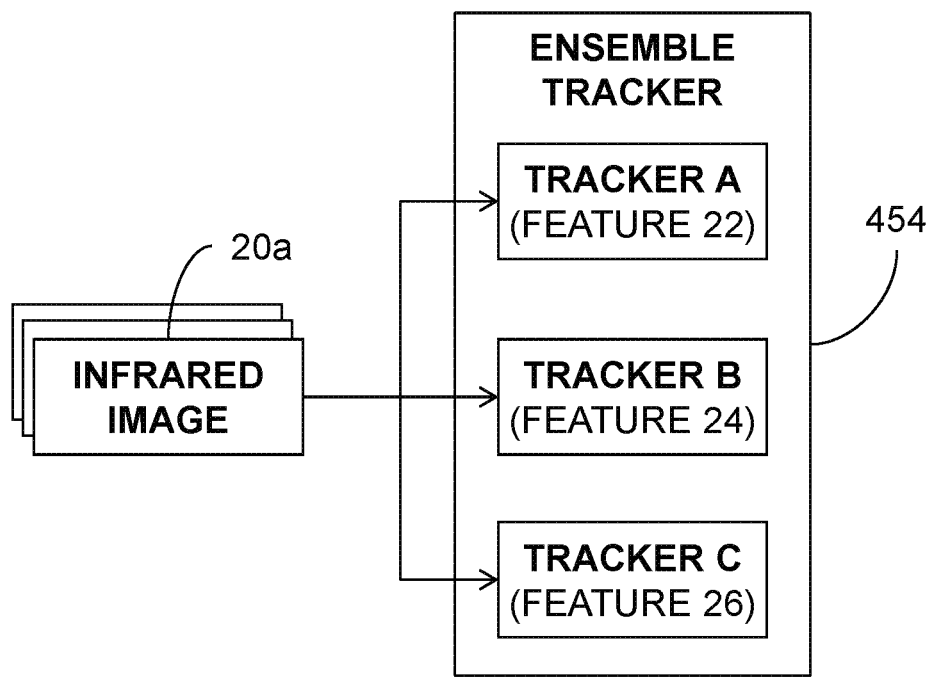
FIG. 4 illustrates an example approach that employs an ensemble tracker to track and process multiple features in captured images of an eye for an eye tracking system, according to aspects of the present disclosure.

The eye tracking system 250 may include an ensemble tracker 454 as shown in FIG. 4. In particular, the ensemble tracker 454, as implemented by the controller(s) 120, employs a tracker A, a tracker B, and a tracker C to process infrared images 20a captured by a high-speed infrared camera. All three trackers A, B, C operate very rapidly using local pixel information, and can work concurrently. Frame-to-frame motion estimates for the eye can be obtained very rapidly (e.g., within a few milliseconds) from any one of the trackers A, B, C.

The tracker A is tuned specifically to the image feature 22 (i.e., texture in iris region). The tracker A may employ variants of the Lucas Kanade Tomasi (LKT) feature tracker to estimate multiscale optic flow of a set of feature points in the iris region 3, which are essentially extrema points with high spatial frequency. These feature points are detected at the start of tracking and can be automatically replenished when they are lost due to changes in the scene.

The tracker B is tuned specifically to the image feature 24 (i.e., contrast between iris and pupil). Using the fact that a pupil appears darker than the iris in the infrared images 20a, the tracker B may use optimization techniques to seek a darker shape formed by a collection of pixels in the pupil region 4 surrounded by lighter colored pixels in the iris region 3. The tracker B may employ robust statistics to ignore the bright and saturated pixels occurring due to reflections, e.g., using Huber's M-estimators.

The tracker C is tuned specifically to the image feature 26 (i.e., iris-pupil boundary). The tracker C may detect the circular pupil-iris boundary by fitting a circular or elliptical model to an edge map obtained from the infrared images 20a at a higher scale.

As shown in FIG. 4, an example approach 400 employs an ensemble tracker 454 that coalesces data from the trackers A, B, C to provide more robust, accurate, and efficient estimates of eye motion from the infrared images 20a. For instance, using an ensemble average motion based on information relating to all three image features 22, 24, 26, the ensemble tracker 454 can estimate parameters for the pupil as an indicator of overall eye motion.

The ensemble tracker 454 is highly robust, because the trackers A, B, C are designed to obtain information on orthogonal (non-overlapping) image features in the images 20a and provide independent estimates of eye motion. These independent estimates are analyzed against each other using a high-level meta-heuristic process to reduce error variance and allow a smooth estimate of eye motion to be obtained with greater accuracy. Occasionally, the trackers A, B, C may fail when tracking becomes challenging due to reflections and other obstructions as shown in FIGS. 9A-E. The high-level meta-heuristic process, however, can account for erroneous and missing information from such failures, thereby allowing tracking to continue.

The ensemble tracker 454 efficiently models characteristic motions occurring in the eye 1. The motion of the eye 1 ranges from high-speed ballistic motions called saccadic movements to slow and smooth pursuit movements used to track a moving object at low velocities. The eye 1 may also be subject to vestibulo-ocular and opto-kinetic reflexes when the angle of gaze is repositioned. Additionally, the eye 1 may be subject to vergence movements when an object is maintained in the center of the field of view of both eyes as the object moves in depth (e.g., along the z-axis shown in FIG. 1). The ensemble tracker 454 is sufficiently rapid and robust to account for anatomic variations in eye geometry, variation in reflectivity of the iris, and variation in contrast of the pupil under these typical motions.

The ensemble tracker 454 accounts for the errors in tracking that might be introduced due to reflections of illumination present during the capture of the images 20. Advantageously, the example approach 400 is not dependent on illumination geometry. For instance, the example approach 400 provides effective eye tracking whether the illumination is provided by a point light source or by an ambient/diffuse light source or whether the light source is on-axis or off-axis. In particular, the example approach 400 can reject the retro-reflections of the light source from the optical surfaces of the eye, i.e., front and back surfaces of the cornea and lens. By using a higher level meta-heuristic to combine the tracking data from the three independent trackers A, B, C, error variance of estimates relating to motion is reduced and the accuracy of the tracker is improved and the speed of tracking at can be maintained at super-real-time (i.e., 60 Hz).

Figure 5A:
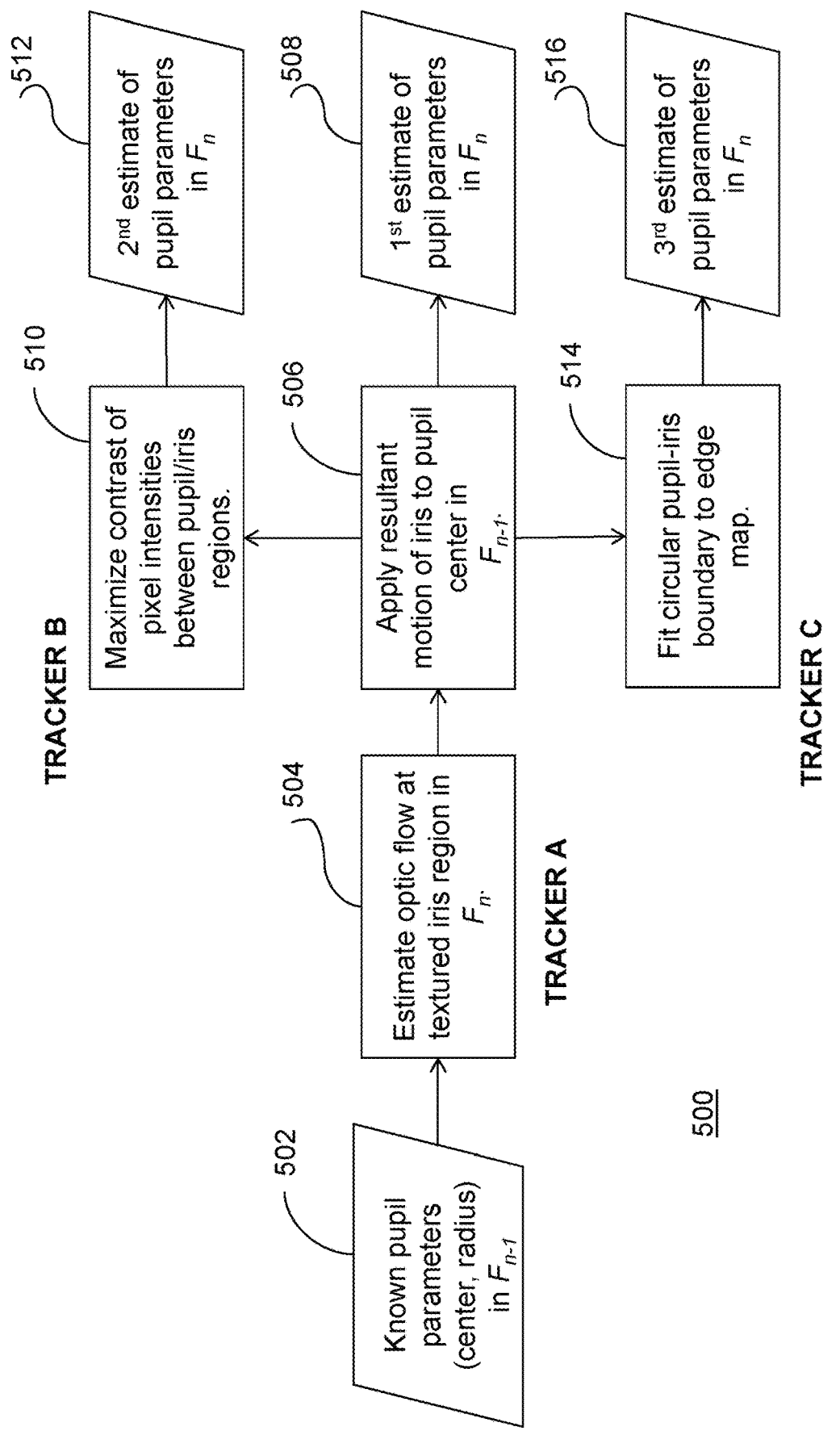
FIGS. 5A-B illustrate an example method employing a higher-level meta-heuristic to coalesce data from three trackers to produce a final estimate relating to eye motion, according to aspects of the present disclosure.
Figure 5B:
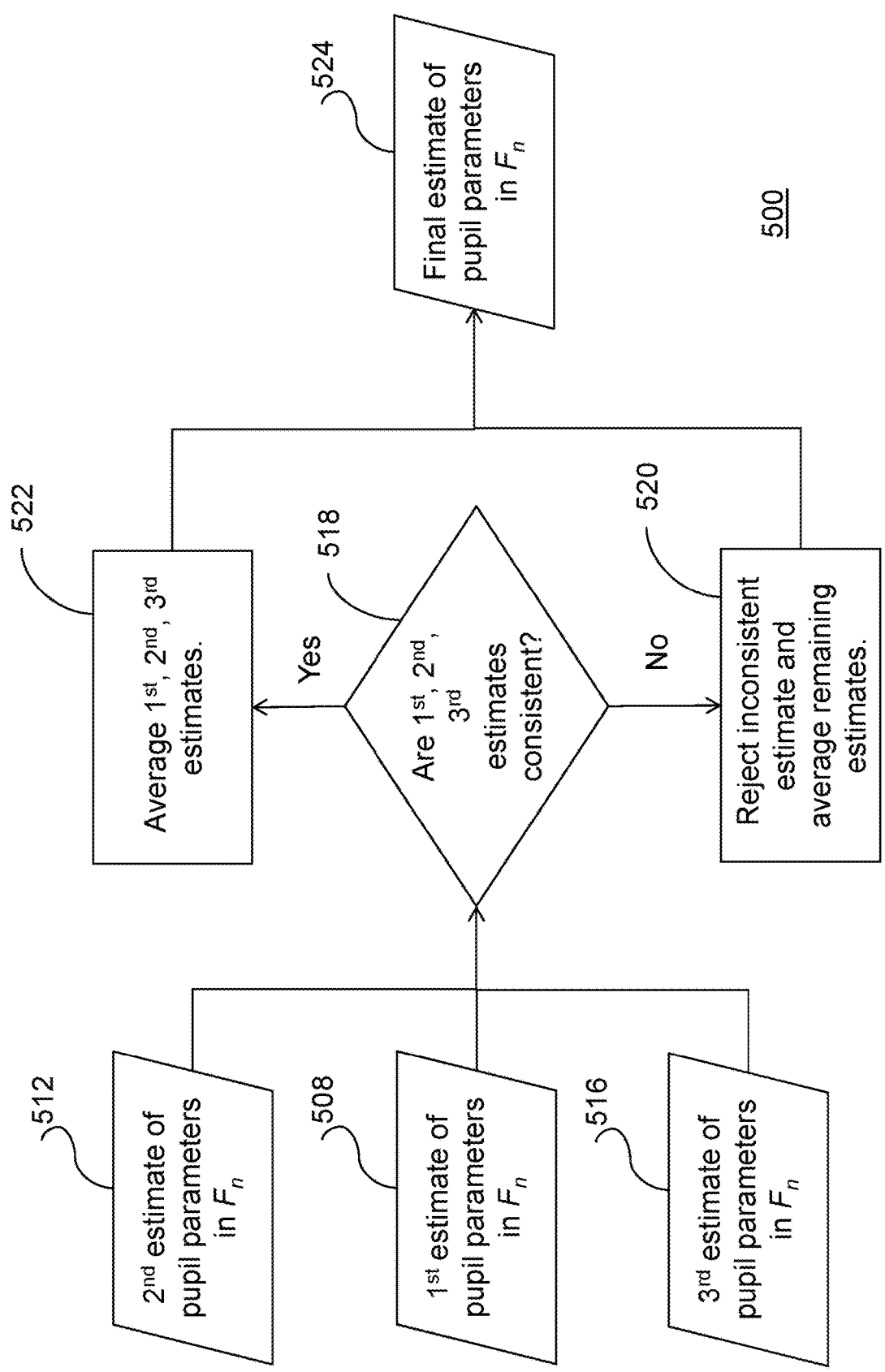

As described above, the trackers A, B, C are designed to obtain information on orthogonal image features in the images 20a, and to provide estimates relating to eye motion, the ensemble tracker 454 employs a higher-level meta-heuristic to manage the trackers A, B, C and coalesce the data from the trackers A, B, C in order to produce a final estimate relating eye motion where net estimation error is minimized. FIGS. 5A-B illustrate an example method 500 employing a higher-level meta-heuristic to produce a final estimate relating to eye motion. The eye motion is expressed in terms of changes in parameters of a pupil of the eye (i.e., pupil center location and pupil radius). A time series of infrared images 20a produces frames $F_i$ that capture the motion of an eye. In the example as illustrated, pupil parameters in a previous frame $F_{n-1}$ (shown as data 502) are known. Tracker A in act 504 employs a multiscale Lucas Kanade Tomasi (LKT) feature tracker to determine an optic flow of a set of feature points, which correspond to texture in an iris region of the present frame $F_n$. A net motion of the pupil correlates to the motion of these feature points and can be determined by combining motion vectors of individual feature points using random sample consensus (RANSAC). In act 506, the resultant motion of the iris (feature points), i.e., the net motion of the pupil, is applied to the pupil center location of the previous frame $F_{n-1}$ to produce a first estimate 508 of the pupil parameters for the present frame $F_n$.

The trackers B and C can be initialized using the first estimate 508 of the pupil center location as an initial guess. In act 510, the tracker B produces a second estimate 512 of the pupil parameters by solving an optimization problem using gradient ascent. In particular, the contrast between pixel intensities in the pupil region and iris region is maximized to determine the unknown pupil center location and radius. Meanwhile, in act 514, the tracker C produces a third estimate 516 of the pupil parameters by fitting a circular pupil-iris boundary to an edge map to determine the unknown pupil center location and radius.

Figure 6:
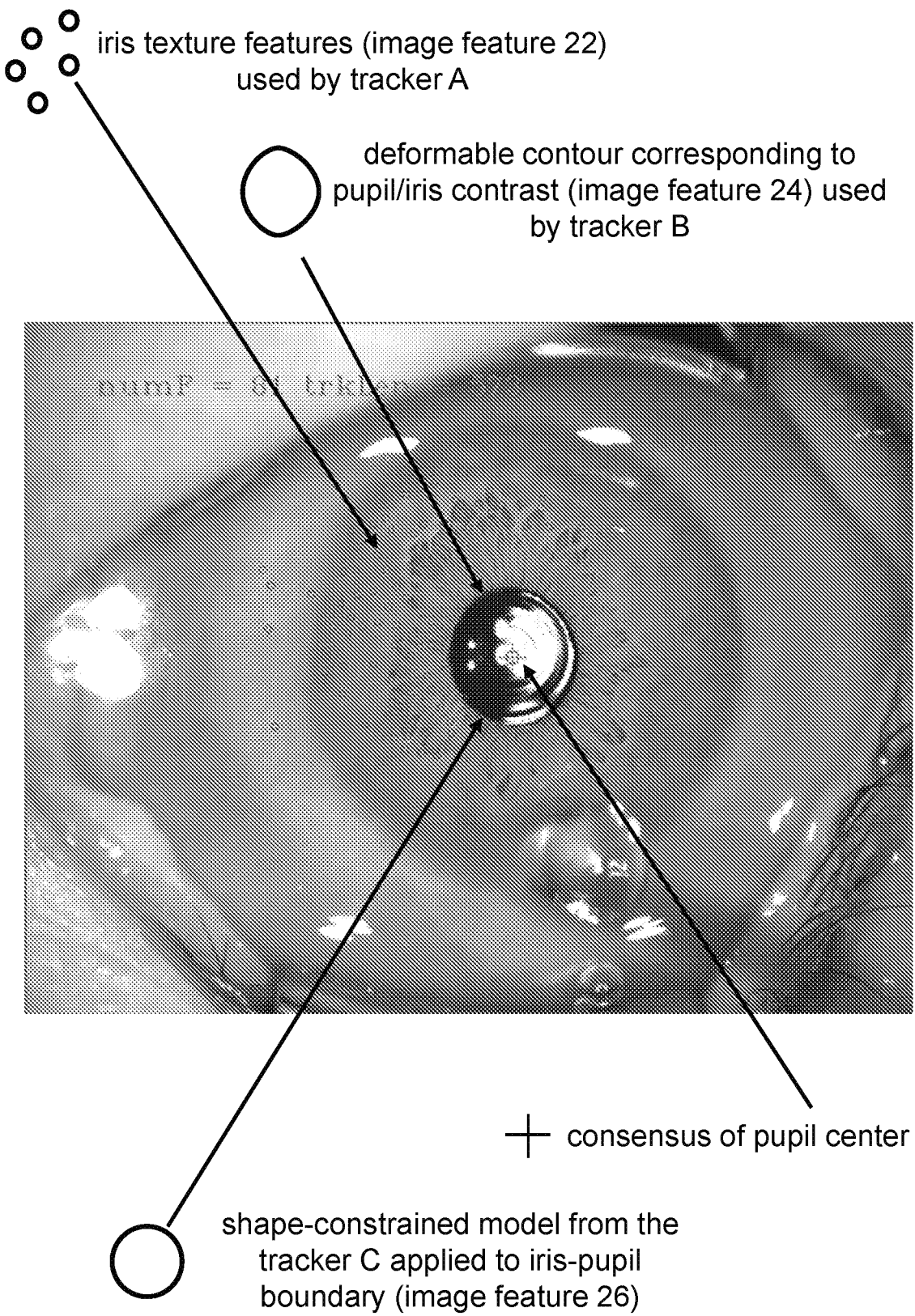
FIG. 6 illustrates an example frame with the image features employed by respective trackers to determine a consensus for a pupil center location based on the example method illustrated in FIGS. 5A-B, according to aspects of the present disclosure.

In decision 518, the estimates 508, 512, 516 of the pupil parameters are evaluated to determine if they are mutually consistent. The higher-level meta-heuristic measures deviation between estimates of the pupil parameters produced by the trackers A, B, C and ranks them based on their consistency. If the least consistent estimate deviates from the other two by an amount greater than an empirical threshold, the one inconsistent estimate is considered erroneous and rejected and the two remaining mutually consistent estimates are averaged in act 520 to produce the final estimate 524 of the pupil parameters in the frame $F_n$. Otherwise, if the least consistent estimate is within the empirical bound, the estimates 508, 512, 516 are considered to be mutually consistent and are then combined by averaging the estimates 508, 512, 516 in act 522 to produce the final estimate 524 of the pupil parameters in the frame $F_n$. FIG. 6 illustrates an example frame with the image features 22, 24, 26 employed by the trackers A, B, C, respectively, and the consensus for the location of the center of the pupil based on the final estimate 524.

In summary, the trackers A, B, C are designed so that most of the useful information in the images is utilized. Each tracker aims at a specific image feature that is mutually exclusive and non-overlapping with the image feature used by other trackers. The approach thus obtains multiple measurements using orthogonal pieces of information, and then robustly combines (coalesces) these measurements to reduce errors due to bad measurement of any one feature. In this way, a failure of any one feature does not affect the tracker at all, and the error variance is always reduced due to averaging.

Figure 9C:
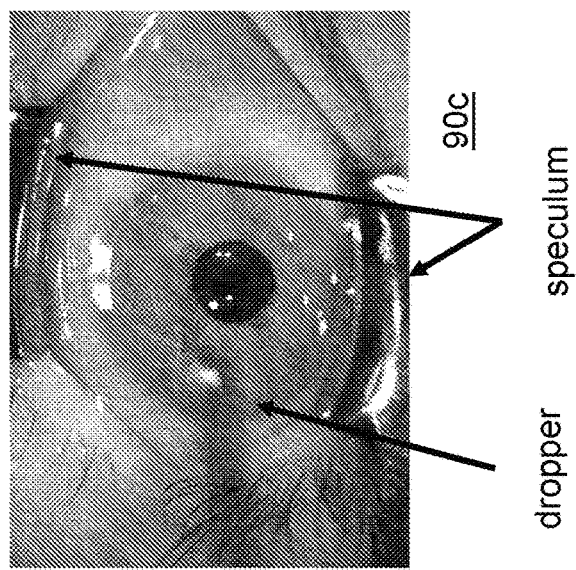
FIG. 9C illustrates an example image capturing a dropper and a speculum used for treatment as a possible error-inducing phenomenon.
Figure 9B:
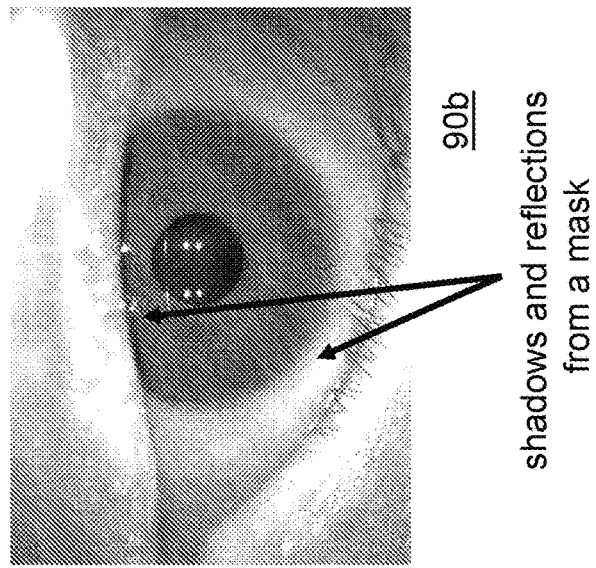
FIG. 9B illustrates an example image capturing shadows and reflections from a mask worn by the patient for treatment or partial obstruction of an eye by an eyelid as a possible error-inducing phenomenon.
Figure 9A:
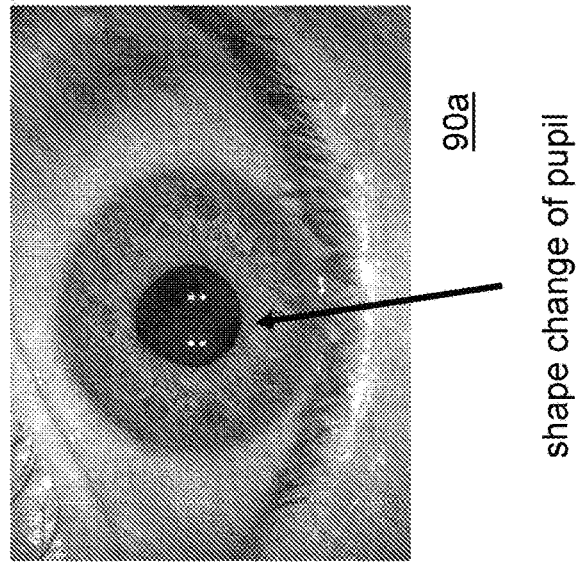
FIG. 9A illustrates an example image capturing an irregularly-shaped pupil or change in shape of a pupil as a possible error-inducing phenomenon.

FIGS. 9A-F illustrate various example phenomena that might be captured in the images 20a and produce aberrations, noise, distortions, occlusions, etc., which can affect the estimates 508, 512, 516 produced by the trackers A, B, C. Such phenomena may induce errors and result in inconsistencies between the estimates 508, 512, 516 as described above. Specifically, FIG. 9A illustrates an image 90a capturing an irregularly-shaped pupil or change in shape of a pupil. FIG. 9B illustrates an image 90b capturing shadows and reflections from a mask worn by the patient for treatment or partial obstruction of an eye by an eyelid. FIG. 9C illustrates an image 90c capturing a dropper and a speculum used for treatment. FIG. 9D illustrates an image 90d capturing graying of a pupil caused by an intra-ocular implant. FIG. 9E illustrates an image 90e capturing an erratic reflection pattern due to an implanted IOL. FIG. 9F illustrates an image 90d capturing an occlusion, such as a finger or an eye dropper.

The higher-level meta-heuristic as shown in FIG. 5 determines an amount of consistency between the estimates 508, 512, 516 from the trackers A, B, C, respectively, and attempts to reduce errors by analyzing them against each other. If the error at a given frame $F_n$ is small, the estimates 508, 512, 516 will be substantially identical with very small mutual deviation, and as such, should provide an indication of the actual pupil parameters (i.e., center location and radius). On the other hand, if the error at a given frame $F_n$ is non-negligible, the estimates 508, 512, 516 will be mutually inconsistent and will reveal deviations from the actual pupil parameters. The inconsistency appears because the trackers A, B, C by design encode orthogonal information by measuring non-overlapping image features, and the same error is likely to be manifested differently by the trackers A, B, C.

Figure 7:
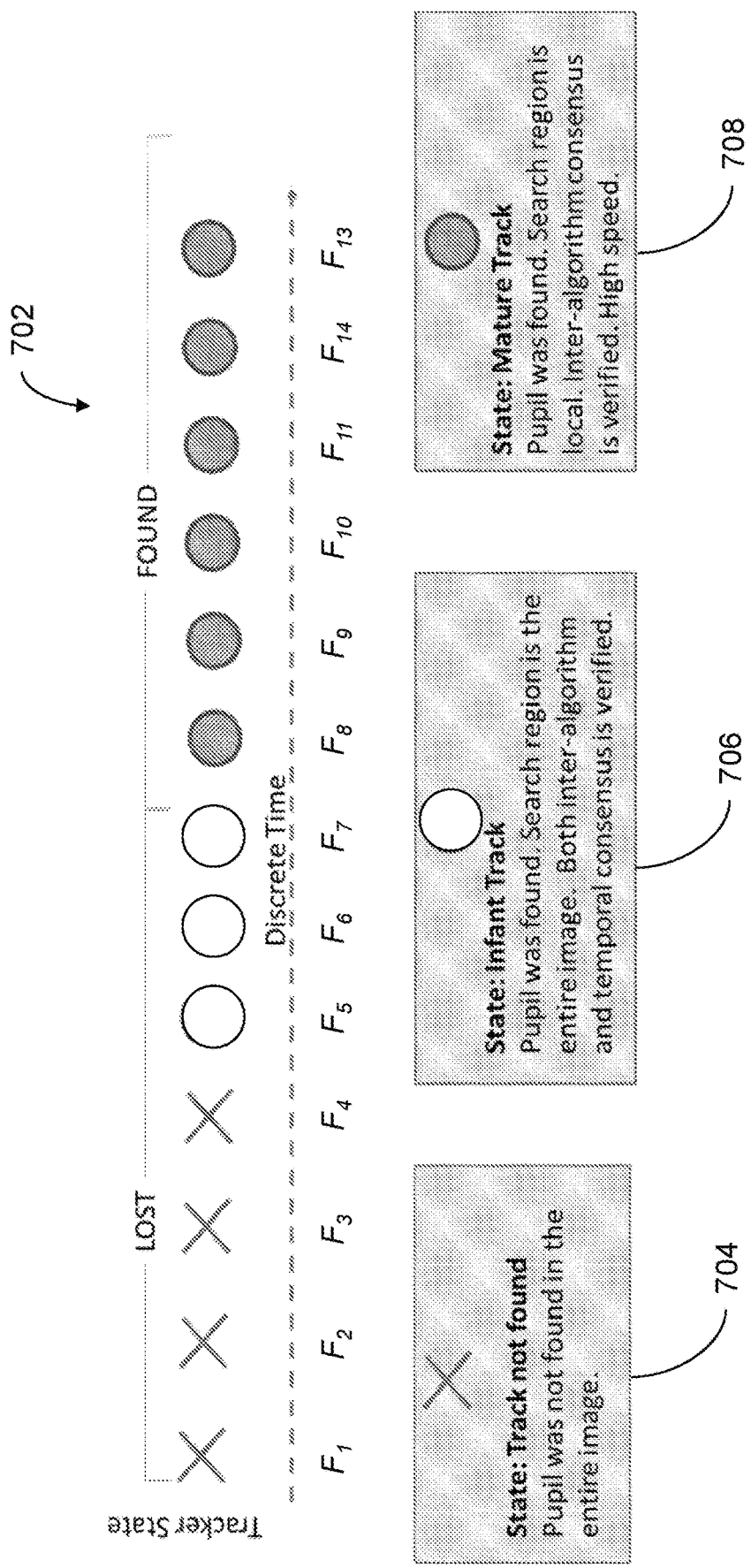
FIG. 7 illustrates an example eye tracking process that produces a track which progresses through various states as a time series of frames $F_i$ is processed, according to aspects of the present disclosure.

As illustrated in FIG. 7, the eye tracking process above can produce a track 702 that progresses through various states as a time series of frames $F_i$ is processed. FIG. 7 shows that as the eye tracking process begins, a pupil cannot be found in the images of initial frames $F_1$, $F_2$, $F_3$, $F_4$. Thus, these initial frames fall under a state 704 designated as "Track Not Found." Once the pupil can be found in the images, the track 702 is considered to be in a state 706 designated as "Infant Track" until certain criteria described below are satisfied. Frames $F_5$, $F_6$, $F_7$ correspond to the period when the track 702 is in the Infant Track state. Once the criteria are satisfied, the track 702 is considered to be in a state 708 designated as "Mature Track." Frame $F_8$ and subsequent frames correspond to the period when the track 702 is in the Mature Track state.

When the track 702 is in the Infant Track state, the processing of the corresponding frames is slower and more exhaustive to ensure that the track 702 is truly established and to avoid false starts. In particular, the entire image of each frame is searched (global search) independently to obtain separate estimates of pupil parameters. As such, the estimates of consecutive frames can be analyzed against each other to verify temporal consistency across frames at the early stages of the track 702. The frames are subjected to this slower, more exhaustive process until temporal consistency is established for an empirical threshold number (N) of frames. The track 702 enters the Mature Track state once this temporal consistency is established. If the consistency check fails at any point, the process restarts and the track 702 cannot be considered to be in the Mature Track state until N consecutive frames are found to be consistent.

Once the track 702 enters the Mature Track state, the frames can be processed according to the example method 500. As described above, the pupil estimates 502 at the previous frame $F_{n-1}$ are used in the processing of the current frame $F_n$ as an initial guess for a relatively narrow search for pupil parameters according to the trackers A, B, C. During the Mature Track state, temporal consistency is not checked because the pupil parameters in the previous frame $F_{n-1}$ are used as an initial guess in the present frame $F_n$. Because temporal consistency is not checked and the searching is local, the tracking process during this state is faster.

Figure 8:
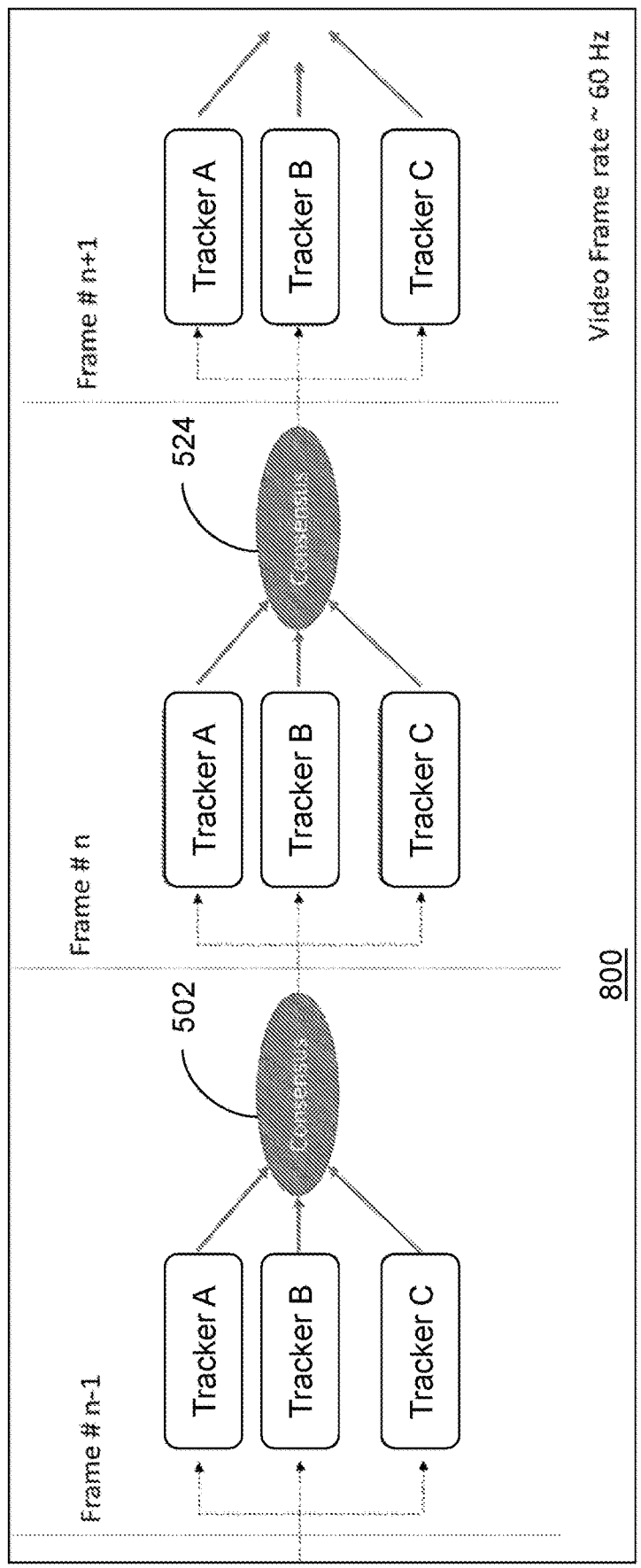
FIG. 8 illustrates an example approach for processing a series of frames $F_i$ with a Mature Track as shown in FIG. 7, according to aspects of the present disclosure.

FIG. 8 illustrates a general approach 800 for processing a series of frames $F_i$ when the track is in the Mature Track state. Specifically, the pupil parameters 502 are determined for the frame $F_{n-1}$ based on a consensus produced by the application of the higher-level meta-heuristic to the trackers A, B, C. As described above, the pupil parameters 524 are determined for the frame $F_n$ based on another consensus produced by the application of the higher-level meta-heuristic to the trackers A, B, C, starting with the pupil parameters 502 from the frame $F_{n-1}$. The processing employed for the frame $F_n$ is repeated for the following frames. For instance, the pupil parameters are determined for the frame $F_{n+1}$ based on yet another consensus produced by the application of the higher-level meta-heuristic to the trackers A, B, C, starting with the pupil parameters 524 from the frame $F_n$. The approach 800 is sufficiently robust and rapid to process frames at a rate of 60 Hz.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored program instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software, or stored program instructions, for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like.

Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure. It is also contemplated that additional embodiments according to aspects of the present disclosure may combine any number of features from any of the embodiments described herein.

What is claimed is:

1. A system for tracking motion of an eye during an eye treatment, comprising:
   an image capture device configured to capture a plurality of images of an eye; and
   one or more controllers including one or more processors configured to execute program instructions stored on one or more computer readable media, the program instructions causing the one or more processors to:
   receive the plurality of images from the image capture device,
   implement a plurality of trackers including a first tracker and a second tracker, each tracker configured to detect a respective feature in the plurality of images and provide, based on the respective feature, a respective set of data relating to motion of the eye, wherein the respective feature detected by the first tracker is orthogonal relative to the respective feature detected by the second tracker and the respective set of data provided by the first tracker is independent of the respective set of data provided by the second tracker;
   identify a state of temporal consistency for a threshold of number of frames in a time series of frames corresponding to the plurality of images based on a track state;
   coalesce the sets of data from the plurality of trackers; and
   determine an indicator of the motion of the eye based on the coalesced sets of data.

2. The system of claim 1, wherein the respective set of data provided by each tracker indicates changes in shape and/or position of the respective feature over the time series of frames corresponding to the plurality of images.

3. The system of claim 1, wherein the indicator of the motion of the eye indicates motion of a pupil of the eye.

4. The system of claim 1, wherein the plurality of images is pixelated and each tracker detects the respective feature based on local pixel information.

5. The system of claim 1, wherein the image capture device includes a high-speed infrared camera and the plurality of images are infrared images.

6. The system of claim 1, wherein, while coalescing the sets of data from the plurality of trackers, the program instructions cause the one or more processors to analyze the sets of data from the plurality of trackers against each other to identify inconsistencies between the sets of data and correct for the inconsistencies in the sets of data.

7. The system of claim 6, wherein the inconsistencies are caused at least by reflections of illumination and/or obstructions captured by the plurality of images.

8. The system of claim 1, wherein the plurality of trackers include:
   a first tracker configured to detect, in the plurality of images, a first feature including anatomical structures in an iris region of the eye and to provide, based on the first feature, a first set of data relating to the motion of the eye;
   a second tracker configured to detect, in the plurality of images, a second feature including a shape defined by a contrast between the iris region and a pupil region of the eye and to provide, based on the second feature, a second set of data relating to the motion of the eye; and
   a third tracker configured to detect, in the plurality of images, a third feature including a boundary between the iris region and a pupil region of the eye and to provide, based on the third feature, a third set of data relating to the motion of the eye.

9. The system of claim 1, wherein to determine the indicator of the motion of the eye, the program instructions cause the one or more processors to process the time series of frames corresponding to the plurality of images by iteratively determining a position of the eye in a frame $F_n$ based on (i) a consensus from the coalesced sets of data from the plurality of trackers for the frame $F_n$, and (ii) the position of the eye determined for a previous frame $F_{n-1}$.

10. A method for tracking motion of an eye during an eye treatment, comprising:
   capturing, with an image capture device, a plurality of images of an eye; and
   implementing, with one or more processors, a plurality of trackers including a first tracker and a second tracker, each tracker configured to detect a respective feature in the plurality of images and provide, based on the respective feature, a respective set of data relating to motion of the eye, wherein the respective feature detected by the first tracker is orthogonal relative to the respective feature detected by the second tracker and the respective set of data provided by the plurality of first tracker is independent of the respective set of data provided by the second tracker;
   identifying, with the one or more processors, a state of temporal consistency for a threshold of number of frames in a time series of frames corresponding to the plurality of images based on a track state;
   coalescing, with the one or more processors, the sets of data from the plurality of trackers; and
   determining, with the one or more processors, an indicator of the motion of the eye based on the coalesced sets of data.

11. The method of claim 10, wherein the respective set of data provided by each tracker indicates changes in shape and/or position of the respective feature over the time series of frames corresponding to the plurality of images.

12. The method of claim 10, wherein the indicator of the motion of the eye indicates motion of a pupil of the eye.

13. The method of claim 10, wherein the plurality of images is pixelated and each tracker detects the respective feature based on local pixel information.

14. The method of claim 10, wherein the image capture device includes a high-speed infrared camera and the plurality of images are infrared images.

15. The method of claim 10, wherein coalescing the sets of data from the plurality of trackers includes analyzing the sets of data from the plurality of trackers against each other to identify inconsistencies between the sets of data and correct for the inconsistencies in the sets of data.

16. The method of claim 15, wherein the inconsistencies are caused at least by reflections of illumination and/or obstructions captured by the plurality of images.

17. The method of claim 10, wherein the plurality of trackers include:

a first tracker configured to detect, in the plurality of images, a first feature including anatomical structures in an iris region of the eye and to provide, based on the first feature, a first set of data relating to the motion of the eye;

a second tracker configured to detect, in the plurality of images, a second feature including a shape defined by a contrast between the iris region and a pupil region of the eye and to provide, based on the second feature, a second set of data relating to the motion of the eye; and a third tracker configured to detect, in the plurality of images, a third feature including a boundary between the iris region and a pupil region of the eye and to provide, based on the third feature, a third set of data relating to the motion of the eye.

18. The method of claim 10, wherein determining the indicator of the motion of the eye includes processing a time series of frames corresponding to the plurality of images by iteratively determining a position of the eye in a frame $F_n$ based on (i) a consensus from the coalesced sets of data from the plurality of trackers for the frame $F_n$, and (ii) the position of the eye determined for a previous frame $F_{n-1}$.

* * * * *